(12) United States Patent
Wenchell

(10) Patent No.: US 7,582,071 B2
(45) Date of Patent: Sep. 1, 2009

(54) INTRODUCER SEAL ASSEMBLY

(75) Inventor: Thomas Wenchell, Durham, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 461 days.

(21) Appl. No.: 11/091,165

(22) Filed: Mar. 28, 2005

(65) Prior Publication Data

US 2006/0217666 A1 Sep. 28, 2006

(51) Int. Cl.
*A61M 5/178* (2006.01)
*A61M 31/00* (2006.01)
(52) U.S. Cl. .................... 604/167.06; 604/508
(58) Field of Classification Search ............... 606/167, 606/185; 604/167.01–167.06, 506
See application file for complete search history.

(56) References Cited

U.S. PATENT DOCUMENTS

| 4,874,378 | A | | 10/1989 | Hillstead |
| 5,389,080 | A | * | 2/1995 | Yoon ................. 604/167.03 |
| 5,395,342 | A | | 3/1995 | Yoon |
| 5,423,761 | A | | 6/1995 | Hein et al. |
| 5,429,609 | A | | 7/1995 | Yoon |
| 5,478,318 | A | | 12/1995 | Yoon |
| 5,584,847 | A | | 12/1996 | Duluco et al. |
| 5,820,600 | A | | 10/1998 | Carlson et al. |
| 5,865,817 | A | | 2/1999 | Moenning et al. |
| 5,924,976 | A | | 7/1999 | Stelzer et al. |
| 6,036,711 | A | * | 3/2000 | Mozdzierz et al. .......... 606/185 |
| 6,039,725 | A | | 3/2000 | Moenning et al. |
| RE36,702 | E | | 5/2000 | Green et al. |
| 6,086,603 | A | | 7/2000 | Termin et al. |
| 6,162,196 | A | * | 12/2000 | Hart et al. .............. 604/167.02 |
| 6,309,345 | B1 | | 10/2001 | Stelzer et al. |
| 6,832,984 | B2 | | 12/2004 | Stelzer et al. |
| 7,186,265 | B2 | * | 3/2007 | Sharkawy et al. .......... 623/2.38 |
| 2004/0204682 | A1 | | 10/2004 | Smith |
| 2006/0224120 | A1 | | 10/2006 | Smith |

FOREIGN PATENT DOCUMENTS

WO WO0241795 5/2002
WO WO 03/094760 A 11/2003

OTHER PUBLICATIONS

European Search Report for EP 06005183, date of completion Jun. 29, 2006 (11 pgs).
European Search Report for Application No. EP 08253100, dated Dec. 12, 2008.

* cited by examiner

*Primary Examiner*—Aarti Bhatia

(57) ABSTRACT

A unique surgical system and method of use includes a seal assembly which is initially mountable about a surgical instrument. The surgical instrument with mounted seal assembly is thereafter positioned within a cannula assembly. The seal assembly forms a fluid tight seal within the interior of the cannula assembly while also forming a fluid tight seal about the surgical instrument. The seal assembly and the cannula assembly cooperate to permit angulation of the surgical instrument. A magnetic coupling assists in retaining the seal assembly within the cannula assembly.

15 Claims, 6 Drawing Sheets

INTRODUCER SEAL ASSEMBLY

BACKGROUND

1. Technical Field

The present disclosure relates to a sealing apparatus and method for facilitating percutaneous access of a surgical instrument into a body cavity. More particularly, the present disclosure relates to a seal apparatus for forming a fluid tight seal between a surgical instrument and an internal passageway of an access or cannula assembly.

2. Description of the Related Art

Minimally invasive and laparoscopic procedures generally require that any instrumentation inserted into the body is sealed, i.e., provisions must be made to ensure that gases and/or fluids do not enter or exit the body through an endoscopic incision, such as, for example in surgical procedures where the surgical region is insufflated. For such procedures, access to anatomical cavities, such as the peritoneal cavity, is usually accomplished by use of a system incorporating a trocar and cannula assembly. Since the cannula is in direct communication with the interior of the peritoneal cavity, the cannula should be adapted to maintain a fluid tight interface between the abdominal cavity and the outside atmosphere. In view of the need to maintain the atmospheric integrity of the inner area of the cavity, a seal assembly for a cannula, which permits introduction of a wide range of surgical instrumentation and maintains the atmospheric integrity of the inner area of the cavity is desirable. In this regard, there have been a number of attempts in the prior art to achieve such sealing requirements. A difficulty encountered with conventional seal assemblies, however, is the inability of accommodating the wide range of sizes of instrumentation. In addition, angulation and/or manipulation of instrumentation within the cannula often present difficulties with respect to maintaining seal integrity.

SUMMARY

Accordingly, the present disclosure provides a unique surgical system and method of use, including a seal apparatus which is mountable about a surgical instrument. The surgical instrument with mounted seal apparatus is thereafter positioned within a cannula assembly. The seal apparatus forms a fluid tight seal within the interior of the cannula assembly while also forming a fluid tight seal about the surgical instrument.

In one preferred embodiment, the surgical method includes the steps of accessing a body cavity with a surgical portal having a longitudinal passage extending therethrough, mounting a seal apparatus onto an instrument shaft of a surgical instrument whereby the instrument shaft is received within an aperture of the seal apparatus with inner seal portions defining the aperture forming a substantial seal about the instrument shaft, at least partially positioning the instrument shaft with mounted seal apparatus within the longitudinal passage of the surgical portal, and establishing, with the seal apparatus, a substantial seal within the longitudinal passage of the surgical portal. Preferably, the step of establishing includes contacting the seal apparatus with interior surfaces of the surgical portal adjacent the longitudinal passage to form the substantial seal within the longitudinal passage.

The surgical method may further include the step of angulating the instrument shaft within the surgical portal to cause corresponding angulations of the seal apparatus within the surgical portal. Preferably, the seal apparatus defines an arcuate outer surface portion and wherein, during the step of angulating, the arcuate outer surface portion traverses the interior surfaces of the surgical portal while maintaining the substantial seal therewith.

The surgical method may also include the step of magnetically coupling or resiliently coupling the seal apparatus with the interior surfaces of the surgical portal to facilitate retention of the seal apparatus within the surgical portal.

The surgical method may further include the step of substantially closing the longitudinal passage of the surgical portal when the instrument shaft is removed therefrom. The step of substantially closing may include disposing a zero-closure valve within the surgical portal. The zero closure valve is adapted to substantially close in the absence of the instrument shaft of the surgical instrument.

In another embodiment, a surgical instrument and seal system for use with a surgical portal is provided. The system includes a surgical instrument adapted to perform a surgical task and having an elongated shaft, and a seal apparatus mounted to the surgical instrument. The seal apparatus includes inner seal portions defining an aperture therein adapted to receive the elongated shaft of the surgical instrument in substantial sealed relation therewith. The surgical instrument and the mounted seal apparatus are dimensioned and configured to be at least partially positionable within the surgical portal and whereby, upon positioning, the seal apparatus is adapted to form a substantial seal within a longitudinal passageway of the surgical portal. The seal apparatus may define an arcuate outer surface. Preferably, the seal apparatus defines a spherical portion having the arcuate outer surface. More preferably, the seal apparatus is in the general shape of a sphere. The seal apparatus may include one of a magnetic material and a ferromagnetic material.

In another alternate embodiment, a surgical kit is provided. The surgical kit includes a cannula and a removable seal apparatus. The cannula includes a cannula housing and a cannula sleeve extending from the housing. The cannula defines a longitudinal passage extending between the cannula housing and the cannula sleeve. The cannula housing defines an inner surface adjacent the longitudinal passage within the cannula housing. The cannula sleeve is adapted to access an underlying body cavity insufflated with gases. The instrument is at least partially positionable within the cannula housing. The seal apparatus includes an outer portion defining an outer arcuate surface and an inner portion defining an aperture for seal reception of a surgical instrument. Upon at least partial positioning of the seal apparatus within the cannula housing, the outer arcuate surface of the seal apparatus engages the inner surface of the cannula housing in substantial sealed relation therewith.

The surgical kit may also include a surgical instrument adapted to perform a surgical task. The surgical instrument includes an elongated shaft where the seal apparatus is mounted on the elongated shaft.

The cannula may include a zero-closure valve for substantially sealing the longitudinal passage of the cannula in the absence of the surgical instrument.

Magnetic coupling means for facilitating retention of the seal apparatus within the cannula housing may be provided. One of the seal apparatus and the cannula housing includes a magnetic element and wherein the other of the seal apparatus and the cannula housing includes a ferromagnetic material. The magnetic element and the ferromagnetic material cooperate to facilitate retention of the seal apparatus within the cannula housing. Alternatively, resilient coupling means may be provided for facilitating retention of the seal apparatus within the cannula housing.

BRIEF DESCRIPTION OF THE DRAWINGS

The foregoing features of the present disclosure will become more readily apparent and will be better understood by referring to the following detailed description of preferred embodiments, which are described hereinbelow with reference to the drawings wherein.

DETAILED DESCRIPTION OF THE PREFERRED EMBODIMENTS

The surgical system of the present disclosure provides a substantial seal between a body cavity of a patient and the outside atmosphere during an endoscopic or laparoscopic surgical procedure. The surgical system contemplates the introduction and manipulation of endoscopic or laparoscopic instrumentation, and maintains a fluid tight interface about the instrumentation to preserve the atmospheric integrity of a surgical procedure from gas and/or fluid leakage. Examples of instrumentation include clip appliers, graspers, dissectors, retractors, staplers, laser probes, photographic devices, endoscopes and laparoscopes, tubes, and the like. Several of these instruments are disclosed in commonly assigned U.S. Pat. Nos. 6,716,232, 6,450,391, 6,231,565, 6,152,872, 5,938,668, 5,913,870 and 5,860,987, the contents of each of these disclosures being incorporated in their entireties herein by reference. Such instruments will be collectively referred to herein as "instruments or instrumentation". The surgical system of the present disclosure is well adapted to accommodate angular manipulation of the surgical instrument. This feature desirably minimizes the entry and exit of gases and/or fluids to/from the body cavity.

In the following description, as is traditional, the term "proximal" refers to the portion of the instrument closest to the operator while the term "distal" refers to the portion of the instrument remote from the operator.

Figure 1:
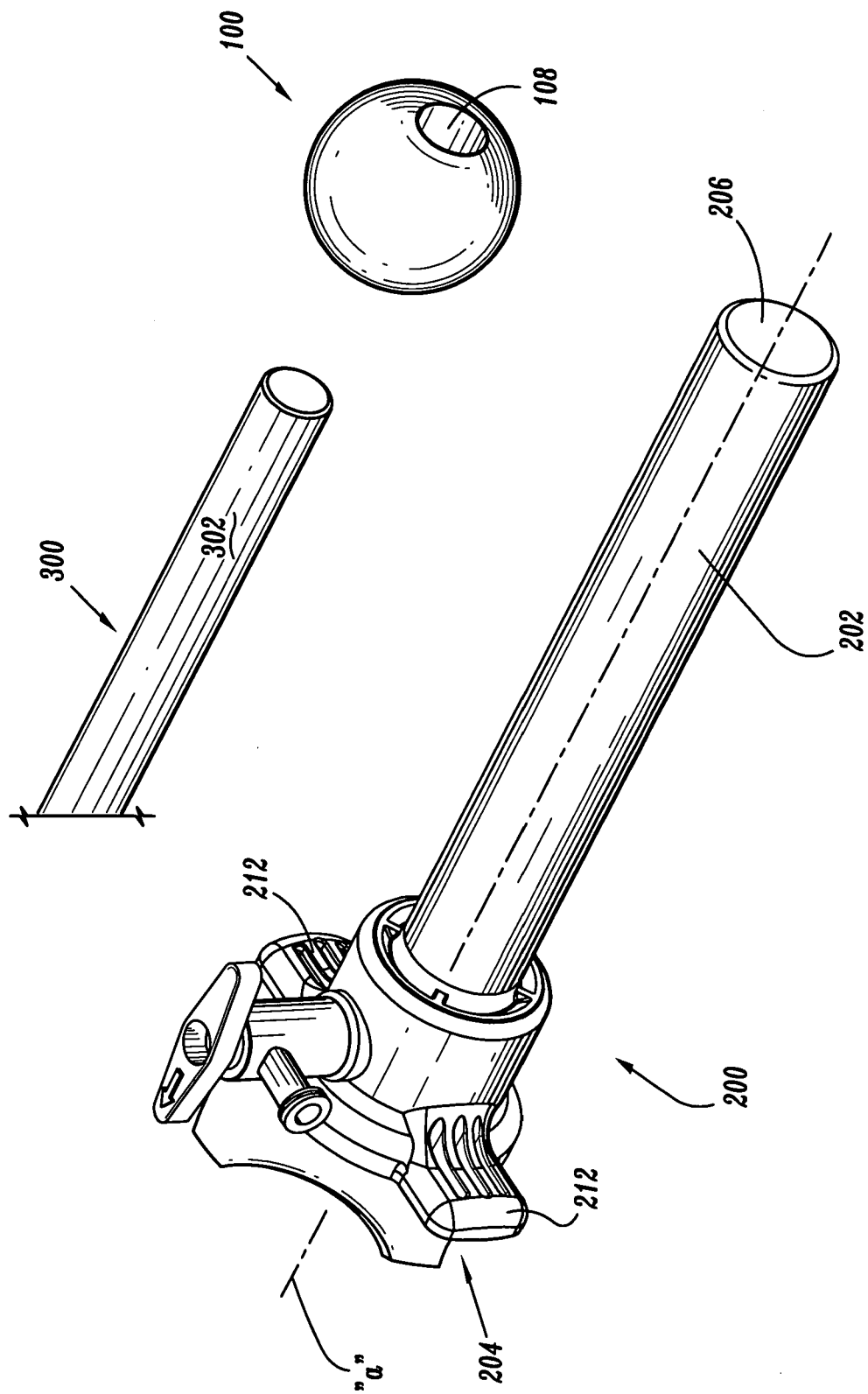
FIG. 1 is a perspective view with parts separated of the surgical system in accordance with the principles of the present disclosure, illustrating the seal assembly, cannula assembly and surgical instrument.
Figure 2:
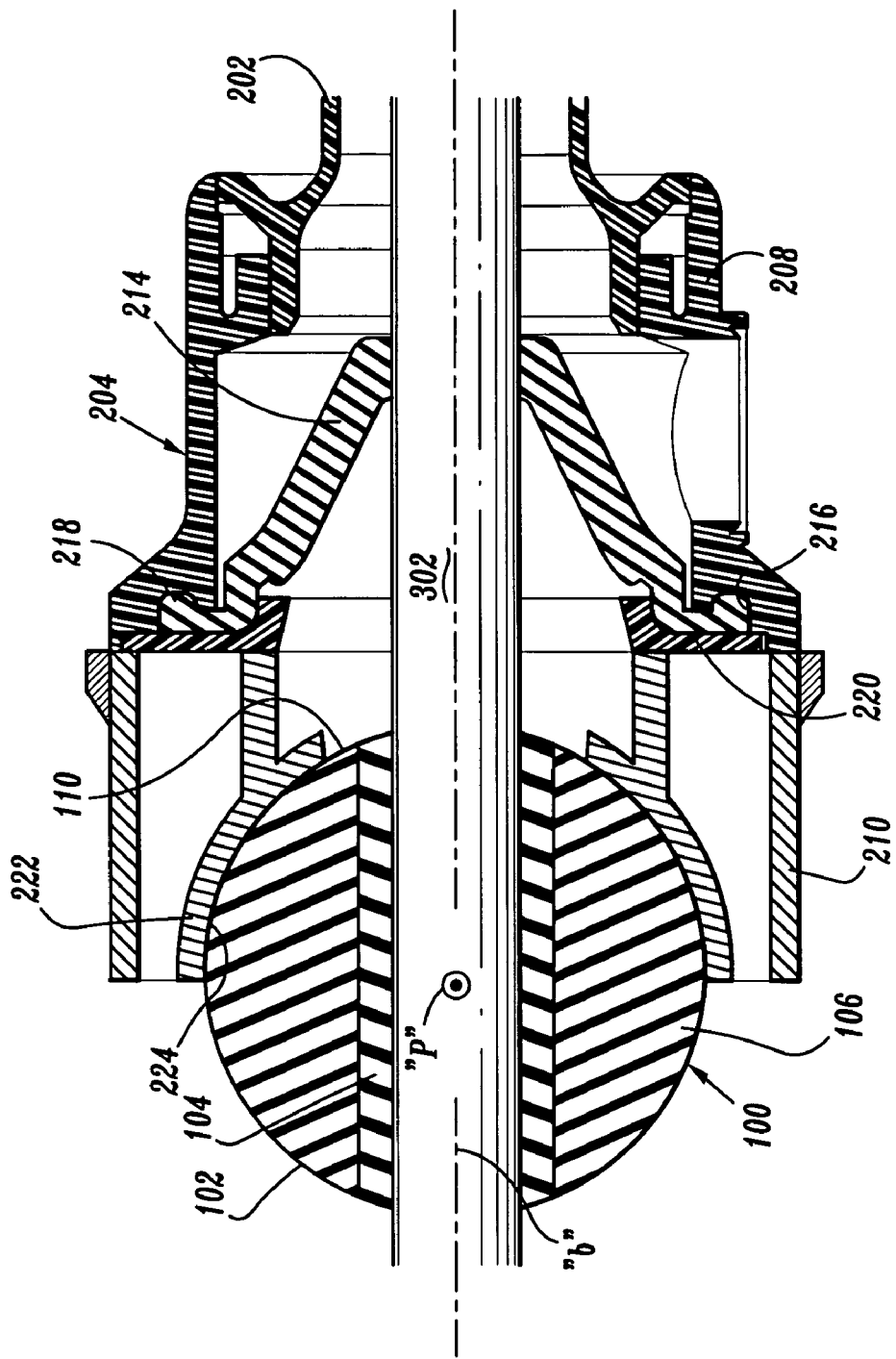
FIG. 2 is an enlarged side cross-sectional view of the surgical system in accordance with the present disclosure illustrating the seal assembly positioned about the surgical instrument and mounted within the cannula assembly.

Referring now to the drawings, in which like reference numerals identify identical or substantially similar parts throughout the several views, FIGS. 1-2 illustrate the surgical system 10 of the present disclosure. Surgical system 10 includes seal assembly 100, cannula assembly 200 and surgical instrument 300. Seal assembly 100 has seal element 102 with an inner portion 104 and an outer portion 106. Inner portion 104 forms a seal and defines aperture 108 which is adapted to receive surgical instrument 300. In one preferred embodiment, inner portion 104 is fabricated from a resilient material whereby portions of the inner portion 104 adjacent aperture 108 engage surgical instrument 300 in fluid tight relation. Suitable materials for inner portion 104 include elastomeric materials such as, e.g., polyisoprene, silicone, rubber, urethane, soft urethane gel, silicon gel, etc. Preferably, the selected material has compressible characteristics to permit inner portion 104 to conform and form a substantial seal about the outer surface of the instrument 300 during manipulation about the operative site. The inner portion 104 and/or outer portion 106 may comprise a compressible foam. It is further envisioned that inner portion 104, outer portion 106 or both, may be a bladder or balloon filled with fluids such as water, saline, gel, etc....

Outer portion 106 may comprise an elastomeric material or, in one embodiment, include a magnetic material or a ferromagnetic metal. In another embodiment, outer portion 106 may be coated with a magnetic coating or a coating of a ferromagnetic material. The use of magnetic material and/or ferromagnetic material facilitates the establishment of a magnetic coupling to assist in removably retaining seal assembly 100 within cannula assembly 200. The magnetic coupling will be discussed in greater detail hereinbelow. It is also envisioned that outer portion 106 may be fabricated from an elastomeric material and be monolithically formed with inner portion 104. Inner portion 104 and outer portion 106 may be fabricated from the same or different material. In certain embodiments, inner portion 104 is formed from an elastomeric material whereas outer portion 106 is formed from a relatively rigid polymeric material.

Figure 3:
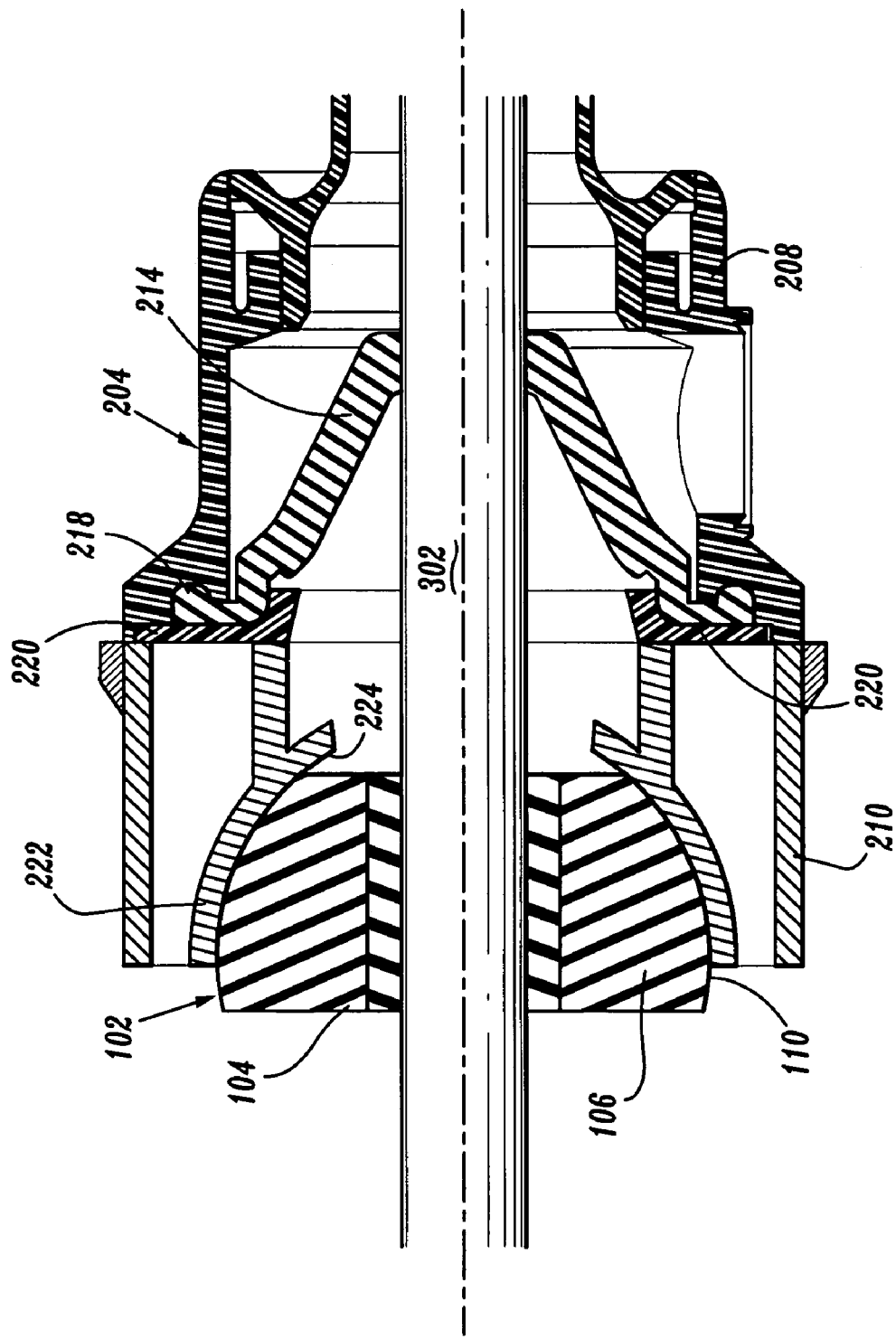
FIG. 3 is an enlarged side cross-sectional view similar to the view of FIG. 2 illustrating an alternate embodiment of the seal assembly.

In the embodiment shown in FIG. 2, outer portion 106 is generally spherical and has a cylindrical opening 103 in which inner portion 104 is disposed. Inner portion 104 has a generally cylindrical shape forming aperture 108 for receipt of surgical instrument 300. Outer portion 106 and inner portion 104 may have other shapes, such as elliptical, polygonal, partially truncated sphere or elliptoid, etc. The spherical shape facilitates removable coupling of seal assembly 100 with cannula assembly 200. It is also envisioned that seal element 102 may be a partial or truncated sphere as shown in FIG. 3.

With continued reference to FIGS. 1-2, outer portion 106 has an outer surface 110 which is arcuate. As to be appreciated, the arcuate configuration of outer surface 110 of seal element 102 permits the seal element 102 to angulate within cannula assembly 200.

Seal assembly 100 is preferably mountable about surgical instrument 300 preferably, about elongated shaft 302 of the instrument, with the elongated shaft 302 being received within aperture 108 of seal element 202. Such mounting is preferably performed prior to positioning seal assembly 100 within cannula assembly 200. Once seal assembly 100 and the instrument 300 are positioned within cannula assembly 200, seal element 102 forms a substantial fluid tight seal within the internal structure of cannula assembly 200 to prevent or substantially minimize the passage of fluids through the cannula assembly.

Referring still to FIGS. 1-2, cannula assembly 200 of the surgical system 10 will be described. Cannula assembly 200 is intended to access a body cavity and permit introduction of instruments required to perform the desired surgical procedure at a remote tissue site. Cannula assembly 200 is particularly adapted for use in laparoscopic surgery where the peritoneal cavity is insufflated with a suitable gas, e.g., $CO_2$, to raise the cavity wall from the internal organs therein. Cannula assembly 200 is typically used with a trocar obturator (not shown) which is a sharp pointed instrument positionable within the passageway of the cannula assembly 200. The trocar obturator is utilized to penetrate the abdominal wall and is then subsequently removed from the cannula assembly 200 to permit introduction of the surgical instrumentation utilized to perform the procedure. In the alternative, a blunt obturator may be used, such as, for example, in a Hasson technique. Semi blunt or dilating obturators may also be used to gain access to the abdominal cavity.

Cannula assembly 200 includes cannula sleeve 202 and cannula housing 204 mounted to a proximal end of the sleeve 202. Cannula sleeve 202 defines a longitudinal axis "a" extending along the length of sleeve 202. Sleeve 202 further defines an internal longitudinal passage 206 dimensioned to permit passage of surgical instrumentation. Sleeve 202 may be formed of stainless steel or other rigid materials, including polymeric materials that are medical grade material, such as surgical steel, titanium, polycarbonate, etc. Sleeve 202 may be clear or opaque. The diameter of sleeve 202 may vary, but, typically ranges from 10 to 15 mm for use with the seal assembly 100 of the present disclosure.

In one preferred embodiment, cannula housing 204 includes two components, specifically, main housing 208 which is attached to the proximal end of cannula sleeve 202 and seal housing 210. Seal housing 210 may be connectable to main housing 208 through a bayonet coupling, a snap fit coupling, ultrasonic welding or any other means envisioned by one skilled in the art including, e.g., adhesive means. Alternatively, seal housing 210 and main housing 208 may be formed integrally with one another. Main housing 208 further includes diametrically opposed housing grips 212 (FIG. 1) dimensioned and arranged for gripping engagement by the fingers of the user. Although shown and described as two components, cannula housing 204 may be a single component and attached to cannula sleeve 202 by any of the aforementioned means or may incorporate multiple components.

With reference to FIG. 3, in conjunction with FIGS. 1-2, main housing 208 further includes duck bill or zero closure valve 214 which tapers distally and inwardly to a sealed configuration as shown. Valve 214 opens to permit passage of the surgical instrument 300 and closes in the absence of the instrumentation and/or in response to the pressurized gases communicating from the insufflated body cavity. Other zero closure valves are also contemplated including single or multiple slit valve arrangements, trumpet valves, flapper valves, etc. Valve 214 may be secured within main housing 208 by any conventional means. In one embodiment, main housing 208 includes internal circumferential recess 216 which receives the outer peripheral flange 218 of valve 214. A valve mount 220 may be positioned to secure the flange area of valve 214 within main housing 208.

Figure 4:
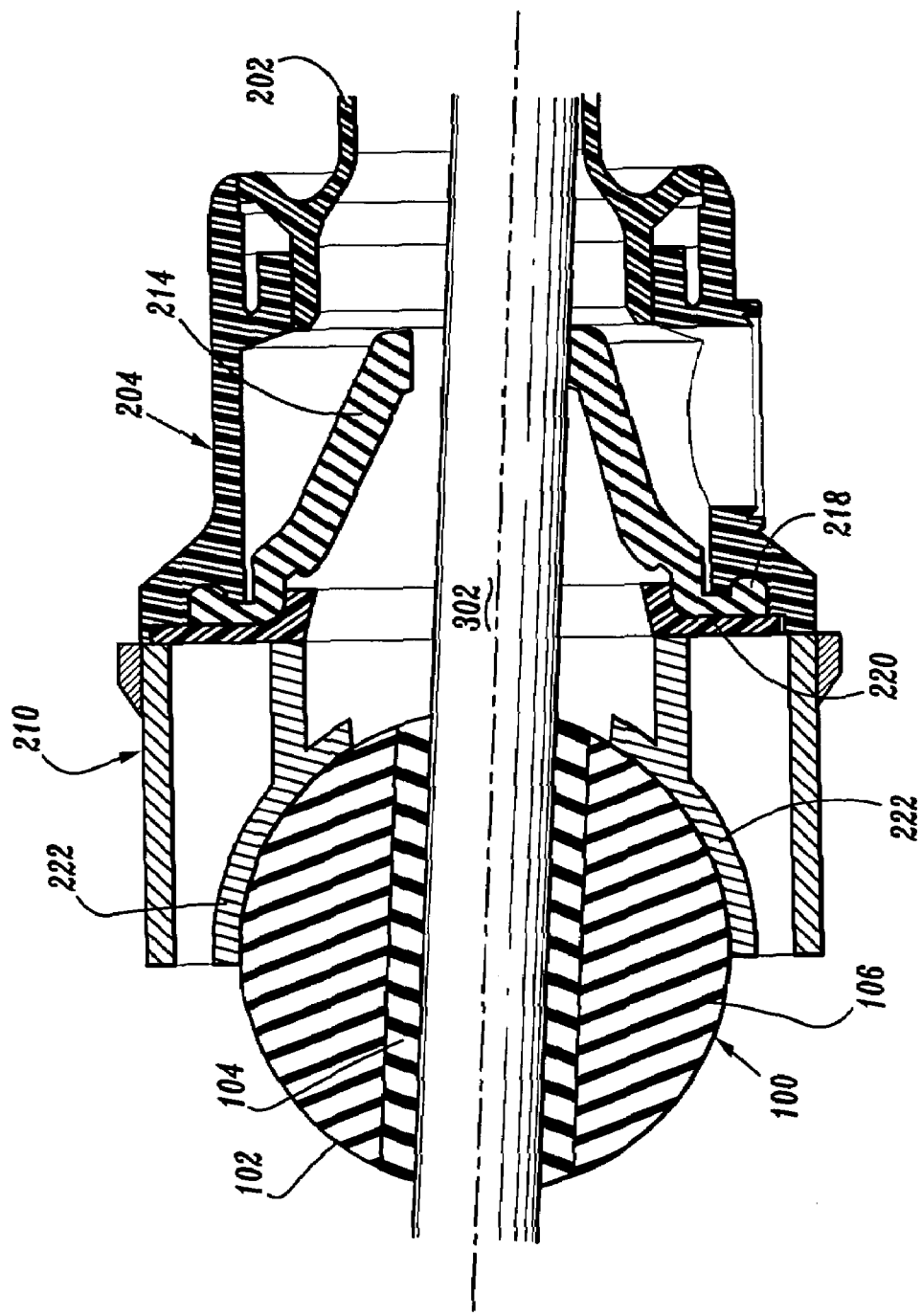
FIG. 4 is an enlarged side cross-sectional view of the surgical system in accordance with the present disclosure illustrating angulation of the surgical instrument and corresponding movement of the seal assembly.

Seal housing 210 has a substantially cylindrical configuration as shown. Seal housing 210 includes seal mount 222 disposed within the interior of the seal housing 210 concentrically arranged about longitudinal axis "a". Seal mount 222 is adapted to support seal assembly 100 in the assembled condition of the components. Seal mount 222 has arcuate support surface 224 defining a concavity as shown. Support surface 224 engages outer surface 110 of seal element 102. In a preferred embodiment, the configuration of arcuate support surface 224 corresponds to the configuration of outer surface 110 of seal element 102. For example, in one preferred embodiment, the radius of curvature of each of arcuate support surface 224 and outer surface 110 of seal element 102 are substantially equivalent. In this regard, seal element 102 is free to swivel or angulate relative to seal mount 220. The term "angulate" is to be interpreted to include at least two types of movement, namely, rotation of seal element 102 about longitudinal axis "b" and pivotal movement of the seal element 102 about a pivot axis "p". FIG. 4 illustrates angulation of seal element 102 during manipulation of surgical instrument 300.

Seal mount 222 preferably is formed of a rigid material such as a metal or polymeric material. Seal mount 222 may have a lubricious coating to facilitate angulation of seal element 102. Similarly, outer surface 110 of seal element 102 may have a lubricious coating. Alternatively, seal mount 222 may have an elastomeric layer defining arcuate support surface 224. Irregardless of the materials utilized, positioning of seal element 102 within seal mount 222 establishes a fluid-tight relation between the seal element 102 and support surface 224, which substantially minimizes passage of gases through cannula assembly 200 during use in a laparoscopic procedure. In one preferred embodiment, seal mount 222 includes a magnetic material or a ferromagnetic material and cooperates with corresponding magnetic or ferromagnetic material at outer surface 110 of seal element 102. In this manner, positioning of seal element 102 within seal mount 222 establishes a magnetic coupling which functions to retain the seal element 102 within the seal mount 222. Preferably, the strength of the magnetic coupling is selectively controlled to permit seal assembly 100 to angulate within seal mount 222 while maintaining the mounted condition of the seal assembly 100 relative to cannula assembly 200. The strength of the magnetic coupling should be selected to allow convenient removal of seal assembly 100 from seal mount 222 while retaining the seal assembly 100 during manipulation. In any of the above, lubricating coatings may be used to further seal the cannula seal housing 210 and facilitate manipulation of instrument.

Surgical system 10 may be part of a surgical kit incorporating at least one seal assembly 100, corresponding cannula assembly 200 and/or surgical instrument 300. For example, the kit could be packaged incorporating a seal assembly 100 and corresponding cannula assembly 200. A plurality of seal assemblies 100 of different sizes (e.g., seal apertures with different diameters) for various instrumentation could be incorporated in the kit. Alternatively, the kit could include surgical instrument 300 and seal assembly 100 with the seal assembly 200 mounted about the surgical instrument 300, either through a permanent or detachable connection.

Figure 5:
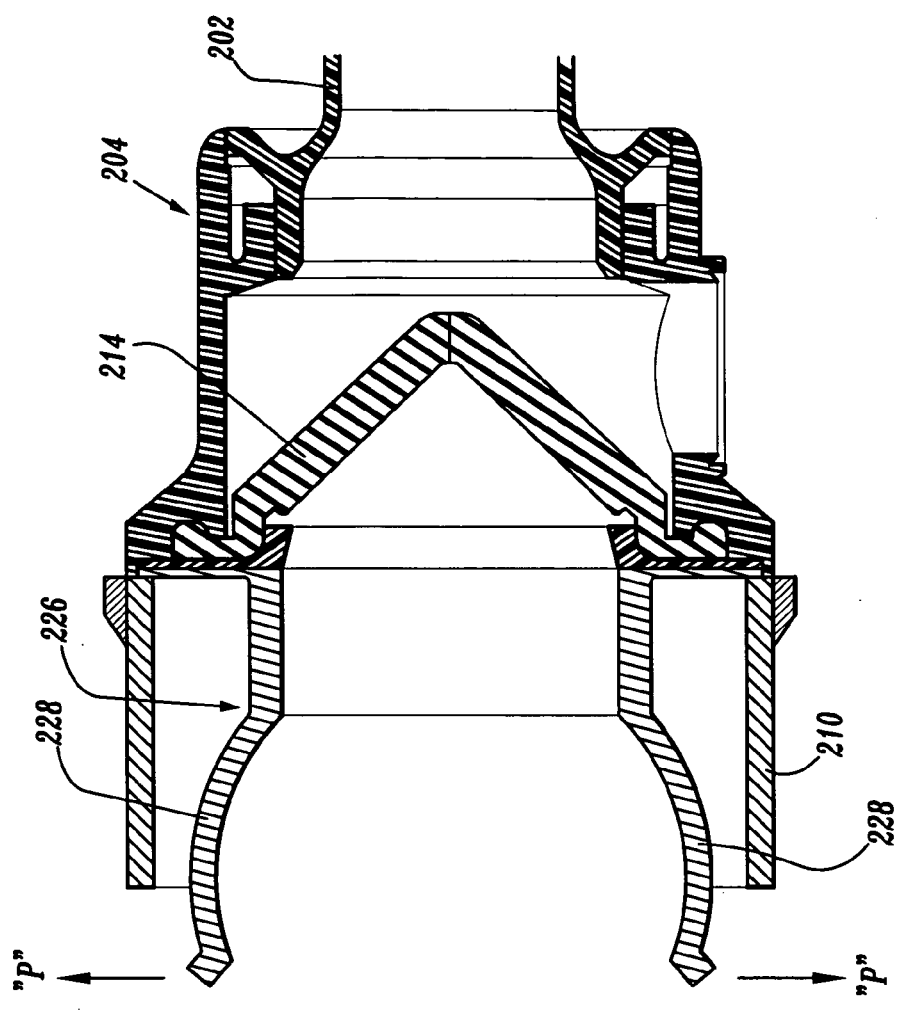
FIG. 5 is an enlarged side cross-sectional view of an alternate embodiment of a surgical system in accordance with the present disclosure illustrating the seal assembly prior to mounting within the cannula assembly.
Figure 5:
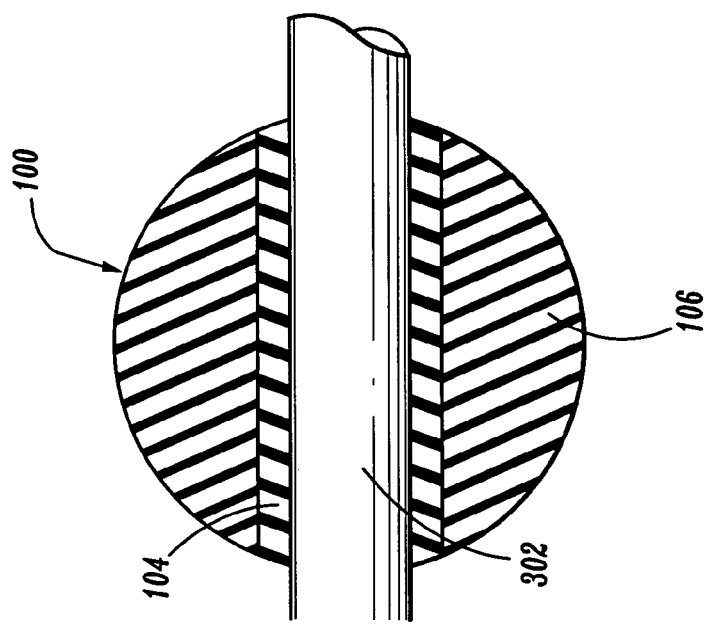
Figure 6:
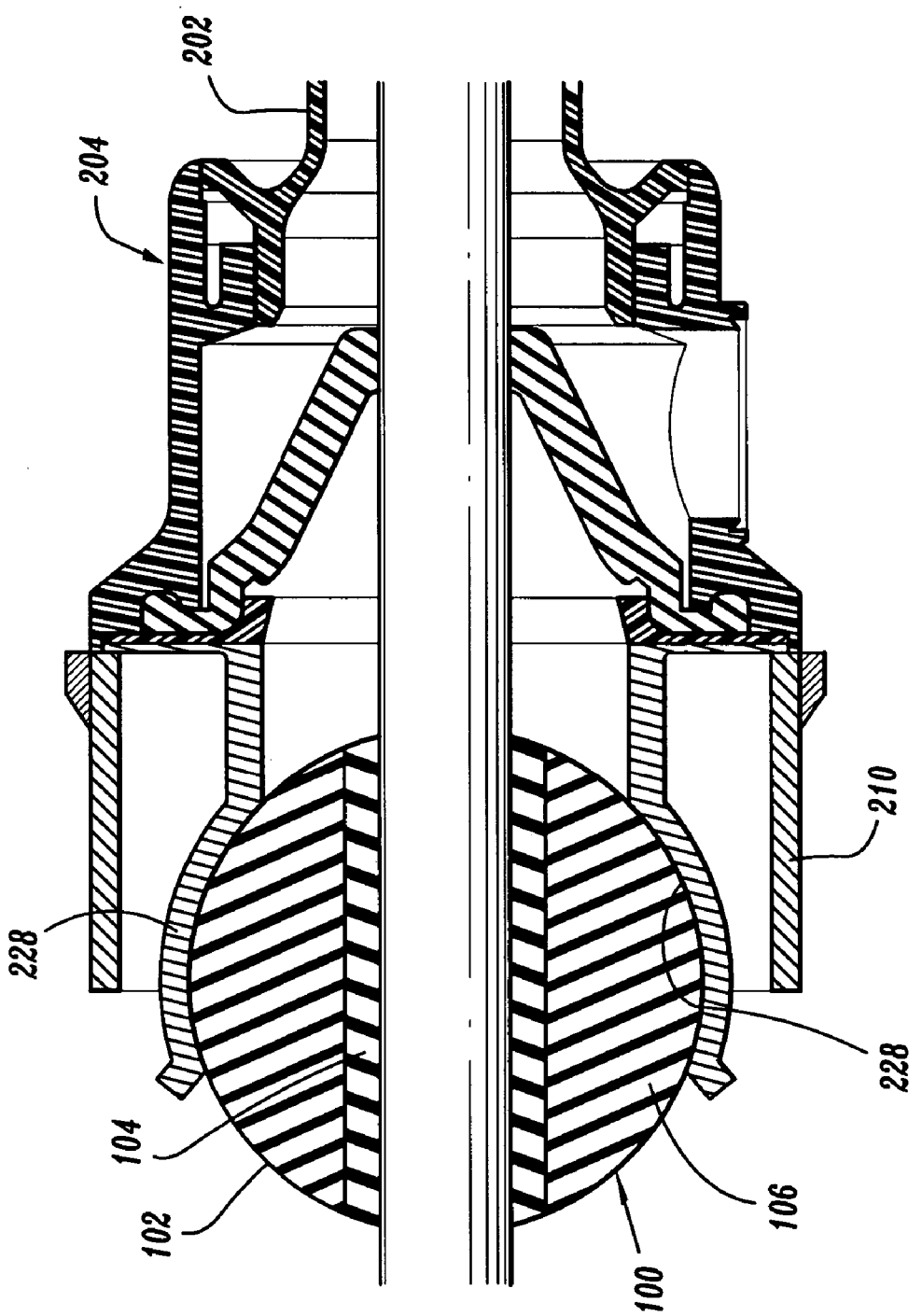
FIG. 6 is an enlarged side cross-sectional view in accordance with the alternate embodiment of FIG. 5 illustrating the seal assembly mounted within the resilient coupling of the cannula assembly.

Referring now to FIGS. 5-6, there is illustrated another embodiment of the present disclosure. This embodiment of surgical system incorporates seal assembly 100 as described hereinabove. Cannula housing 204 includes resilient coupling 226 incorporating first and second resilient legs 228 which receive and mount seal assembly 100 within cannula 200. Resilient legs 228 are adapted to flex or pivot outwardly in the direction of directional arrows "p" to receive seal assembly 100 and then return under the influence of their natural resiliency to retain seal assembly 100 within resilient coupling 226. Resilient legs 228 each include a central arcuate portion 230 defining an arcuate configuration approximating the general arcuate shape of the outer surface 110 of seal element 102. In the mounted condition of seal assembly 100, the seal assembly 100 may angulate within cannula assembly 200 in the manner described in connection with the embodiment of FIGS. 1-4. The contacting surfaces of resilient legs 228 and seal element 102 may incorporate lubricious coatings to facilitate rotational and pivotal movement of the seal assembly 100. Resilient legs 228 may comprise a polymeric material or resilient metal such as spring steel. In other regards, seal assembly 100 is utilized in the aforedescribed manner.

While the invention has been particularly shown, and described with reference to the preferred embodiments, it will be understood by those skilled in the art that various modifications and changes in form and detail may be made therein without departing from the scope and spirit of the invention. Accordingly, modifications such as those suggested above, but not limited thereto, are to be considered within the scope of the invention.

What is claimed is:

1. A surgical method, which comprises:
    accessing a body cavity with a surgical portal having a longitudinal passage extending therethrough;
    mounting a seal apparatus onto an instrument shaft of a surgical instrument whereby the instrument shaft is received within an aperture of the seal apparatus with inner seal portions defining the aperture forming a substantial seal about the instrument shaft;
    subsequent to the step of mounting the seal apparatus onto the instrument, at least partially positioning the instrument shaft within the longitudinal passage of the surgical portal; and
    establishing, with the seal apparatus, a substantial seal within the longitudinal passage of the surgical portal, wherein the step of establishing includes introducing the seal apparatus within a pair of resilient external mounting legs of the surgical portal whereby the mounting legs secure the seal apparatus.

2. The surgical method according to claim 1 including the step of accessing a body cavity insufflated with gas.

3. The surgical method according to claim 1 wherein the step of introducing includes displacing the mounting legs move from an initial position to a radial outward position to permit passage of the seal apparatus and, thereafter, permitting the mounting legs to return toward the initial position, to thereby permit the mounting legs to cooperatively engage the seal apparatus to releasably retain the seal apparatus within the mounting legs.

4. The surgical method according to claim 1 wherein the step of establishing includes contacting the seal apparatus with interior surfaces of the surgical portal adjacent the longitudinal passage to form the substantial seal within the longitudinal passage.

5. The surgical method according to claim 4 including the step of resiliently coupling the seal apparatus with the interior surfaces of the surgical portal.

6. The surgical method according to claim 4 including the step of magnetically coupling the seal apparatus with the interior surfaces of the surgical portal.

7. The surgical method according to claim 4 including the step of angulating the instrument shaft within the surgical portal to cause corresponding angulations of the seal apparatus within the surgical portal.

8. The surgical method according to claim 7 wherein the seal apparatus defines an arcuate outer surface portion and wherein, during the step of angulating, the arcuate outer surface portion traverses the interior surfaces of the surgical portal while maintaining the substantial seal therewith.

9. The surgical method according to claim 7 including the step of substantially closing the longitudinal passage of the surgical portal when the instrument shaft is removed therefrom.

10. The surgical method according to claim 9 wherein the step of substantially closing includes disposing a zero-closure valve within the surgical portal, the zero closure valve adapted to substantially close in the absence of the instrument shaft of the surgical instrument.

11. A surgical kit, which comprises:
    a cannula including a cannula housing and a cannula sleeve distally extending from the housing, the cannula defining a longitudinal axis and having a longitudinal passage extending between the cannula housing and the cannula sleeve, the cannula sleeve adapted to access an underlying body cavity insufflated with gases;
    a pair of internal mounting legs at least partially disposed within the cannula housing and depending therefrom, the mounting legs adapted to move from an initial position to a radial outward position relative to the longitudinal axis, each mounting leg defining an inner mounting surface adjacent the longitudinal passage within the cannula housing, and a seal apparatus adapted to be received within the internal mounting legs, the seal apparatus including an outer seal segment and an inner seal segment defining a passage for sealed reception of a surgical instrument, the outer seal segment including an outer mounting surface and being dimensioned whereby, upon positioning of the seal apparatus within the internal mounting legs, the mounting legs move from the initial position to the radial outward position to permit passage of the seal apparatus and, thereafter, return to the initial position, to thereby permit the inner mounting surfaces of the mounting legs to cooperatively engage the outer mounting surface of the outer seal segment to releasably retain the seal apparatus within the mounting legs.

12. The surgical kit according to claim 11 wherein the outer mounting surface of the seal apparatus and the inner mounting surfaces of the mounting legs are generally arcuate, and are adapted to cooperate to permit angulation of the seal apparatus within the mounting legs relative to the longitudinal axis.

13. The surgical kit according to claim 11 wherein the mounting legs are adapted for pivotal movement to move between the initial position and the radial outward position.

14. The surgical kit according to claim 11 including a surgical instrument adapted to perform a surgical task, the surgical instrument including an elongated shaft and having the seal apparatus mounted on the elongated shaft.

15. The surgical kit according to claim 11 wherein the cannula includes a zero-closure valve for substantially sealing the longitudinal passage of the cannula in the absence of the surgical instrument.

* * * * *

UNITED STATES PATENT AND TRADEMARK OFFICE
CERTIFICATE OF CORRECTION

PATENT NO. : 7,582,071 B2  Page 1 of 1
APPLICATION NO. : 11/091165
DATED : September 1, 2009
INVENTOR(S) : Thomas Wenchell It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 927 days.

Signed and Sealed this

Fourteenth Day of September, 2010

David J. Kappos
*Director of the United States Patent and Trademark Office*